(12) United States Patent
Pellacini et al.

(10) Patent No.: US 10,143,200 B2
(45) Date of Patent: Dec. 4, 2018

(54) SYNERGISTIC COMPOSITIONS FOR THE PROTECTION OF AGRARIAN CROPS AND THE USE THEREOF

(71) Applicant: STICHTING I-F PRODUCT COLLABORATION, Amsterdam (NL)

(72) Inventors: Franco Pellacini, Milan (IT); Matteo Santino Vazzola, Cogliate (IT); Marilena Gusmeroli, Monza (IT); Entela Sinani, Novara (IT); Manuela Riservato, Novara (IT)

(73) Assignee: STICHTING I-F PRODUCT COLLABORATION, Amsterdam (NL)

( * ) Notice: Subject to any disclaimer, the term of this patent is extended or adjusted under 35 U.S.C. 154(b) by 0 days.

(21) Appl. No.: 14/407,961

(22) PCT Filed: Jun. 13, 2013

(86) PCT No.: PCT/EP2013/062306
§ 371 (c)(1),
(2) Date: Dec. 14, 2014

(87) PCT Pub. No.: WO2013/186325
PCT Pub. Date: Dec. 19, 2013

(65) Prior Publication Data
US 2015/0164076 A1  Jun. 18, 2015

(30) Foreign Application Priority Data
Jun. 15, 2012 (IT) ............................. MI2012A1045

(51) Int. Cl.
| | |
|---|---|
| *A01N 43/56* | (2006.01) |
| *A01N 43/653* | (2006.01) |
| *A01N 37/34* | (2006.01) |
| *A01N 37/50* | (2006.01) |
| *A01N 59/20* | (2006.01) |
| *A01N 37/10* | (2006.01) |
| *A01N 43/54* | (2006.01) |
| *A01N 43/84* | (2006.01) |
| *A01N 47/38* | (2006.01) |
| *A01N 47/40* | (2006.01) |

(52) U.S. Cl.
CPC ............. *A01N 43/56* (2013.01); *A01N 37/10* (2013.01); *A01N 37/34* (2013.01); *A01N 37/50* (2013.01); *A01N 43/54* (2013.01); *A01N 43/653* (2013.01); *A01N 43/84* (2013.01); *A01N 47/38* (2013.01); *A01N 47/40* (2013.01); *A01N 59/20* (2013.01)

(58) Field of Classification Search
CPC .......................... A01N 2300/00; A01N 43/56
See application file for complete search history.

(56) References Cited

U.S. PATENT DOCUMENTS

| | | | |
|---|---|---|---|
| 4,742,074 A | 5/1988 | Nishida | |
| 5,093,347 A | 3/1992 | Graneto | |
| 5,498,624 A | 3/1996 | McLoughlin | |
| 7,470,793 B2 | 12/2008 | Dunkel | |
| 2006/0155122 A1 | 7/2006 | Dunkel | |
| 2010/0197925 A1 | 8/2010 | Desbordes | |

FOREIGN PATENT DOCUMENTS

| | | |
|---|---|---|
| DE | 10250110 A1 | 5/2004 |
| EP | 0199822 A1 | 11/1986 |
| EP | 0256503 A2 | 2/1988 |
| EP | 0276177 A1 | 7/1988 |
| EP | 0280275 A2 | 8/1988 |
| EP | 0569912 A1 | 11/1993 |
| JP | 6296471 A | 5/1987 |
| JP | 6470479 A | 3/1989 |
| JP | 01313402 A | 12/1989 |
| JP | 02157266 A | 6/1990 |
| JP | 2249966 A | 10/1990 |
| JP | 5310512 A | 11/1993 |
| JP | 01117864 A | 5/1999 |
| JP | 2009501742 A | 1/2009 |
| JP | 2011511032 A | 4/2011 |

(Continued)

OTHER PUBLICATIONS

Knittel et al. ("Drug Design and Relationship of Functional Groups to Pharmacological Activity"; David A Williams and Thomas L Lemke; Foye's Principles of Medicinal Chemistry, 5th Edition, 2002; 37-67).*
Hewitt, "New Modes of Action of Fungicides", Pesticide Outlook, Feb. 2000, pp. 28-32.*
Kosman et al. "Procedures for Calculating and Differentiating Synergism and Antagonism in Action of Fungicide Mixtures", Phytopathology, 86(11), 1996, pp. 1263-1272.*
WO1986/002641 Machine Translation, accessed Feb. 6, 2017.*
International Search Report in corresponding application dated Jul. 19, 2013.

(Continued)

*Primary Examiner* — Kortney L. Klinkel
(74) *Attorney, Agent, or Firm* — Hedman & Costigan, P.C.; James V. Costigan; Kathleen A. Costigan

(57) ABSTRACT

Synergistic compositions comprising:
one component (A), consisting of the compound having formula (I) 3-difluoromethyl-N-(7-fluoro-1,1,3-trimethyl-4-indanyl)-1-methyl-4-pyrazolecarboxamide

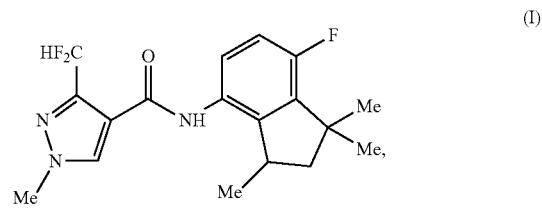

one or more components (B) having a fungicidal or insecticidal activity, and their use for the control of of harmful insects in agrarian crops.

16 Claims, No Drawings

(56) References Cited

FOREIGN PATENT DOCUMENTS

| JP | 2011511033 | A | | 4/2011 | | |
|---|---|---|---|---|---|---|
| WO | 8602641 | A1 | | 5/1986 | | |
| WO | WO1986/002641 | | * | 5/1986 | | |
| WO | 01/53259 | A1 | | 7/2001 | | |
| WO | 2004/018438 | A2 | | 3/2004 | | |
| WO | 2004/072023 | A2 | | 8/2004 | | |
| WO | 2004/103975 | A1 | | 12/2004 | | |
| WO | 2005/075452 | A1 | | 8/2005 | | |
| WO | WO 2009/098218 | | * | 8/2009 | | |
| WO | 2011/135833 | A1 | | 11/2011 | | |
| WO | WO2011/135833 | | * | 11/2011 | | |
| WO | 2012055674 | A1 | | 5/2012 | | |
| WO | WO 2012/084812 | | * | 6/2012 | ........... | C07D 231/14 |
| WO | 2013186325 | A1 | | 12/2013 | | |

OTHER PUBLICATIONS

Erickson, JA et al., Hydrogen Bond Donor Properties of the Difluoromethyl Group, J. Org. Chem. 1995, 60, 1626-1631.
Jerry March, Advanced Organic Chemistry, 1992, John Wiley & Sons, pp. 417-424; 392-402.
International Search Report in corresponding application PCT/EP2011/073225, dated Feb. 3, 2012.
English Translation of Columbian Patent Office Action dated Dec. 16, 2014.
Jeschke, P., "The Unique Role of Halogen Substituents in the Design of Modern Agrochemicals" Pest Manag. Sci. 2010, 66, 10-10-27, Published online Aug. 21, 2009.
Chinese Patent Office Action in corresponding application dated Nov. 17, 2015.
Japanese patent Office Action in corresponding application dated Aug. 1, 2016 (with Translation of the Examiner's comments).

* cited by examiner

SYNERGISTIC COMPOSITIONS FOR THE PROTECTION OF AGRARIAN CROPS AND THE USE THEREOF

The present invention relates to synergistic compositions for the protection of agricultural crops and use thereof.

In particular, object of the present invention are compositions comprising one compound belonging to the N-indanyl-pyrazolecarboxamides chemical class and one or more fungicidal or insecticidal compounds.

In the application of antiparasitic products for agricultural use, it is widely known to combine two or more products having a different mechanism of action and/or a different biological target, in order to broaden the action range of the mixtures with respect to the product used individually and to prevent the occurrence of resistance phenomena from the harmful organisms, phenomena which with time tend to reduce the effectiveness of the antiparasitic products used.

Compositions of fungicidal N-indanyl-1-methyl-3-(halo)alkyl-4-pyrazolecarboxamides with fungicidal or insecticidal compounds such as azoles, strobilurins, acylalanines, phenylpyrroles, chlorothalonil, dithiocarbamates, abamectin, insecticidal diamides, neonicotinoids, sulfoxaflor, pyrethroids, carbamates, phenylpyrazoles, are described in the patent applications WO 2011/135833, WO 2011/135835, WO 2011/135836, WO 2011/135837, WO 2011/135838, WO 2011/135839, WO 2011/135827, WO 2011/135828, WO 2011/135830, WO 2011/135831, WO 2011/135832, WO 2011/135834, WO 2011/135840.

The applicant has now surprisingly found that combining one specific fungicidal compound belonging to the class of N-indanyl-pyrazolecarboxamides with one or more compounds selected from a series of compounds having fungicidal or insecticidal activity, compositions are obtained having biological activities which are:
1) improved with respect to those expected on the basis of the activities of the products used alone;
2) superior to those achievable with the compositions disclosed in said prior art documents.

A first object of the present invention therefore relates to synergistic compositions for the protection of agricultural crops comprising:

at least a component [A] consisting of the compound of formula (I) 3-difluoromethyl-N-(7-fluoro-1,1,3-trimethyl-4-indanyl)-1-methyl-4-pyrazolecarboxamide

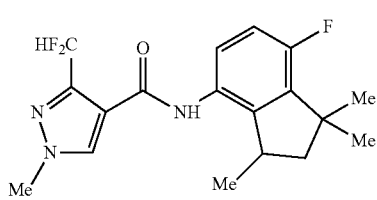

(I)

wherein Me represents a methyl group $CH_3—$, at least a component [B] selected from fungicidal or insecticidal compounds belonging to one or more of the following groups of fungicidal and insecticidal compounds:
fungicidal compounds:
i) azoles;
ii) amino-derivatives;
iii) strobilurins;
iv) specific anti-oidium compounds;
v) aniline-pyrimidines;
vi) benzimidazoles and analogues;
vii) dicarboximides;
viii) polyhalogenated fungicides;
ix) systemic acquired resistance (SAR) inductors;
x) phenylpyrroles;
xi) acylalanines;
xii) anti-peronosporic compounds;
xiii) dithiocarbamates;
xiv) arylamidines;
xv) phosphorous acid and its derivatives;
xvi) fungicidal copper compounds;
xvii) fungicidal amides;
xviii) nitrogen heterocycles;
insecticidal compounds:
xix) neonicotinoids;
xx) phenylpyrazoles;
xxi) pyrethroids;
xxii) carbamates;
xxiii) macrolides of microbial origin;
xxiv) insecticidal diamides;
xxv) trifluoromethylpyridyl derivatives.

The compound of formula (I) can be prepared:
1) by acid isomerization of N-(3-difluoromethyl-1-methyl-1H-4-pyrazolecarbonyl)-6-fluoro-2,2,4-trimethyl-1,2,3,4-tetrahydro-quinoline (II), according to reaction scheme 1, and as described in Example 1:

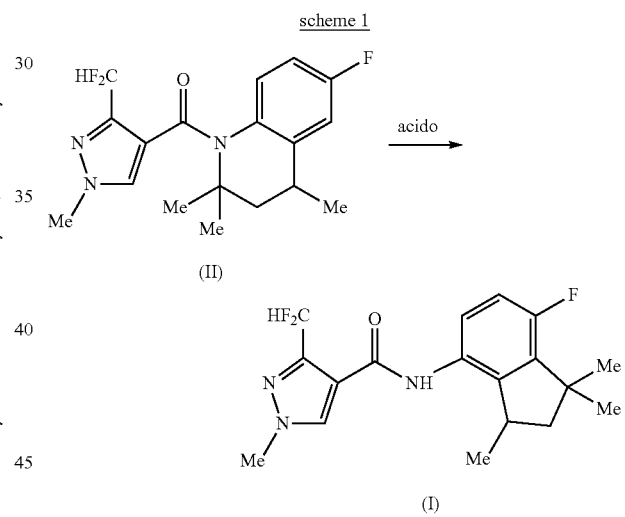

2) by condensation of 3-difluoromethyl-1-methyl-1H-pyrazole-4-carboxylic acid or its derivative, of general formula (III), with 7-fluoro-1,1,3-trimethyl-4-aminoindane (IV), utilizing methods well known in organic chemistry, according to scheme 2:

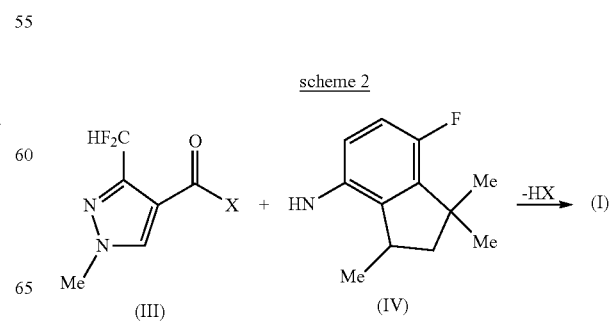

wherein X represents a group selected from OH, alkoxy $C_1$-$C_6$ or a halogen atom (preferably chlorine).

The intermediate of formula (II) is in turn obtained by condensation of a compound of general formula (III) with 6-fluoro-2,2,4-trimethyl-1,2,3,4-tetrahydroquinoline (V), according to scheme 3:

scheme 3

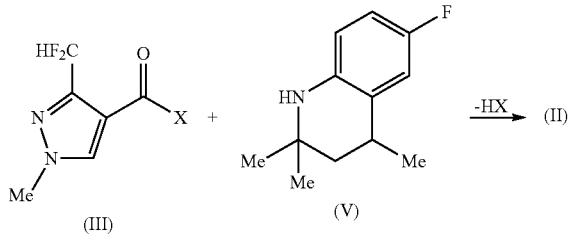

wherein X represents a group selected from OH, alkoxy $C_1$-$C_6$ or a halogen atom (preferably chlorine).

The 3-difluoromethyl-1-methyl-1H-pyrazole-4-carboxylic acid and its derivatives of general formula (III) are known products, described for example in the U.S. Pat. No. 5,093,347.

The intermediate of formula (V) can be prepared, according to reaction scheme 4, by hydrogenation of 6-fluoro-2,2,4-trimethyl-1,2-dihydroquinoline (VI), in turn obtained according to a method described in Organic Synthesis, Coll. Vol. III, pag. 329, starting from acetone and 4-fluoroaniline:

scheme 4

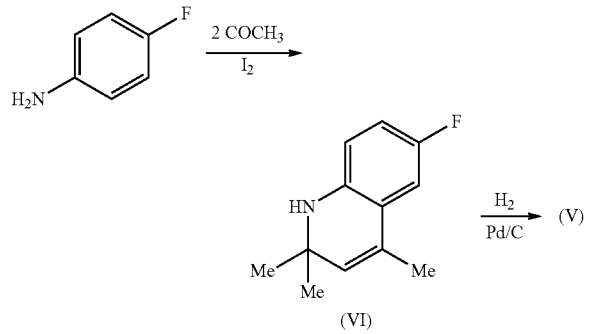

in the aforesaid formulas (I)-(VI) Me represents a methyl group $CH_3-$.

The aminoindane of formula (IV) can be prepared, analogously to what described in the patent N. EP 0654464, by condensation of 6-fluoro-2,2,4-trimethyl-1,2-dihydroquinoline (VI) with a carboxylic acid or its derivative, hydrogenation on Pd/C, isomerization with sulfuric acid and hydrolysis of the amide bond with water in acetic acid.

The compound of formula (I) contains an asymmetric carbon atom in position 3 of the indanyl group and it is usually obtained as racemic mixture of the two enantiomers having configurations R and S (molar ratio R:S equal to 1:1). However, it is possible to prepare mixtures of the two enantiomers of the compound of formula (I) wherein the ratio R:S is different from 1:1 (enriched mixtures).

Moreover, it is possible to prepare the single enantiomers R and S of the compound of formula (I) in substantially pure form (>99.99% by weight).

The aforesaid enantiomeric enriched mixtures and the substantially pure single enantiomers can be prepared, for example, by condensing the compounds of general formula (III) with enriched or enantiomerically pure forms (substantially pure single enantiomers) of the aminoindane of formula (IV), according to the reaction scheme 2; enriched or enantiomerically pure forms of the aminoindane of formula (IV) can be in turn obtained through enantioselective reactions and/or chemical and/or chromatographic separation of the enantiomers, according to methods described in literature for analogous products, for example as disclosed in the aforesaid EP 0654464.

In the synergistic compositions of the present invention the compound of formula (I) can be a racemic mixture, (I)-RS, or an enriched mixture of one of the two enantiomers, or even a substantially pure specific enantiomer (I)-R or (I)-S.

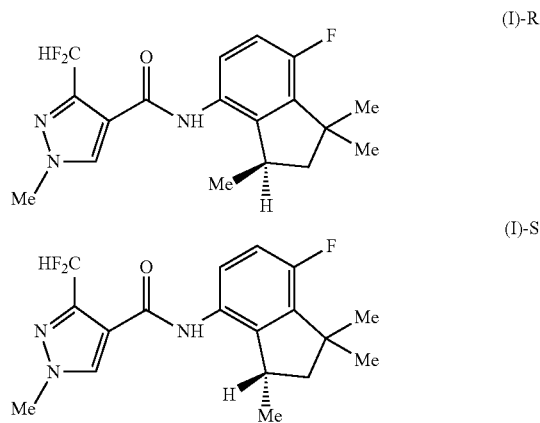

In the case of enriched mixtures of the compound of formula (I), those enriched in the enantiomer R are preferred, preferably with an R:S ratio of the two enantiomers ranging from 51:49 to 99.99:0.01 by weight.

Among the two enantiomeric forms of the compound of formula (I), the substantially pure isomer R is preferred.

The compounds among which to select the component [B] of the synergistic compositions are here indicated with their common international ISO name; their chemical structures and CAS and IUPAC chemical names are reported on the Alan Wood's Website (www.alanwood.net), Compendium of Pesticide Common Names; for most compounds, these features are also reported, together with chemical-physical data and biological features, in the "Pesticide Manual", C. D. S. Tomlin, 15$^{th}$ Edition, 2009, British Crop Production Council Editor.

Examples of fungicidal arylamidines of group xiv are reported in the international patent applications WO 2000/46184, WO 2007/031508, WO 2009/156098.

Components [B] preferred of the compositions object of the present invention are:
i) azoles: azaconazole, bitertanol, bromuconazole, cyproconazole, difenoconazole, epoxyconazole, fenbuconazole, fluquinconazole, flusilazole, flutriafol, hexaconazole, imazalil, ipconazole, metconazole, myclobutanil, penconazole, propiconazole, prochloraz, prothioconazole, simeconazole, tebuconazole, tetra-conazole, triadimefon, triadimenol, triflumizole, triticonazole;
ii) amino-derivatives: aldimorph, dodine, dodemorph, fenpropimorph, fenpropidin, guazatine, iminoctadine, spiroxamine, tridemorph;

iii) strobiluris: azoxystrobin, dimoxystrobin, fluoxastrobin, kresoxim-methyl, metominostrobin, orysastrobin, picoxystrobin, pyraclostrobin, pyrametostrobin, pyraoxostrobin, trifloxystrobin;
iv) specific anti-oidium compounds: cyflufenamid, flutianil, metrafenone, proquinazid, pyriofenone, quinoxyfen;
v) aniline-pyrimidines: pyrimethanil, mepanipyrim, cyprodinil;
vi) benzimidazoles and analogues: benomyl, carbendazim, fuberidazole, thiabendazole, thiophanate-methyl;
vii) dicarboximides: iprodione, procymidone;
viii) polyhalogenated fungicides: chlorothalonil, captan, captafol, folpet, dichlofluanid, tolylfluanid;
ix) SAR inductors: acibenzolar, probenazole, isotianil, tiadinil;
x) phenylpyrroles: fenpiclonil, fludioxonil;
xi) acylalanines: benalaxyl, benalaxyl-M, furalaxyl, metalaxyl, metalaxyl-M;
xii) anti-peronosporic compounds: ametoctradin, amisulbrom, benthiavalicarb, cyazofamid, cymoxanil, dimethomorph, ethaboxam, famoxadone, fenamidone, flumetover, flumorph, fluopicolide, iprovalicarb, mandipropamid, valifenalate;
xiii) dithiocarbamates: maneb, mancozeb, propineb, zineb;
xiv) arylamidines: N-ethyl-N-methyl-N'-{4-[3-(4-chlorobenzyl)-1,2,4-thiadiazolyl-5-oxy]-2,5-xylyl}-formamidine;
xv) phosphorous acid and derivatives: fosetyl-aluminium, potassium phosphite, sodium phosphite, choline phosphite;
xvi) copper fungicides: copper (II) hydroxide, copper oxychloride, copper (II) sulfate, Bordeaux mixture, copper salycilate $C_7H_4O_3.Cu$, cuprous oxide $Cu_2O$;
xvii) fungicidal amides: carpropamid, fenhexamid, silthiofam, zoxamid, bixafen, boscalid, carboxin, fluopicolide, fluopyram, flutolanil, fluxapyroxad, furametpyr, isopyrazam, oxycarboxin, penflufen, penthiopyrad, sedaxane, thifluzamide;
xviii) nitrogen heterocycles: fenpyrazamine, fluazinam, pyribencarb, tebufloquin;
xix) neonicotinoids: acetamiprid, clothianidin, dinotefuran, flupyradifurone, imidacloprid, nitenpyram, thiacloprid, thiametoxam;
xx) phenylpyrazoles: ethiprole, fipronil, flufiprole, pyrafluprole, pyriprole;
xxi) pyrethroids: bifenthrin, beta-cyfluthrin, lambda-cyhalothrin, cypermethrin, deltamethrin, tefluthrin;
xxii) carbamates: oxamyl, thiodicarb, carbosulfan, methiocarb, carbofuran;
xxiii) macrolides of microbial origin: abamectin, emamectin benzoate, spinetoram, spinosad;
xxiv) insecticidal diamides: chlorantraniliprole, cyantraniliprole, flubendiamide;
xxv) trifluoromethylpyridyl derivatives: flonicamid, sulfoxaflor.

Among the aforesaid, components [B] particularly preferred are:
i) cyproconazole, difenoconazole, epoxyconazole, flutriafol, penconazole, prochloraz, prothioconazole, tebuconazole, tetraconazole;
ii) fenpropimorph, spiroxamine;
iii) azoxystrobin, fluoxastrobin, kresoxim-methyl, picoxystrobin, pyraclostrobin, trifloxystrobin;
iv) metrafenone, proquinazid;
v) mepanipyrim, cyprodinil;
vi) iprodione, procymidone;
vii) carbendazim, thiophanate-methyl;
viii) chlorothalonil;

x) fludioxonil;
xi) benalaxyl, benalaxyl-M, metalaxyl-M;
xii) benthiavalicarb, cyazofamid, cymoxanil, dimetomorph, mandipropamid, valifenalate;
xvi) copper (II) hydroxide, copper oxychloride, copper (II) sulfate, copper salycilate $C_7H_4O_3.Cu$, cuprous oxide $Cu_2O$;
xix) clothianidin, imidacloprid, thiachloprid, thiametoxam;
xx) ethiprole, fipronil;
xxi) lambda-cyalothrin, deltamethrin, tefluthrin;
xxiv) chlorantraniliprole, flubendiamide.

The weight ratios of components [A] and [B] in the compositions object of the present invention can vary within a wide range, even depending on the parasites to be controlled and on the single component [B] used (or the plurality of components [B] used), and are usually comprised between 1:20 and 20:1.

Preferred compositions are those comprising at least the following combinations of compounds:
C1: (I)-RS+tetraconazole;
C2: (I)-RS+tebuconazole;
C3: (I)-RS+cyproconazole;
C4: (I)-RS+difenoconazole;
C5: (I)-RS+epoxyconazole;
C6: (I)-RS+flutriafol;
C7: (I)-RS+penconazole;
C8: (I)-RS+prothioconazole;
C9: (I)-RS+prochloraz;
C10: (I)-RS+fenpropimorph;
C11: (I)-RS+spiroxamine;
C12: (I)-RS+azoxystrobin;
C13: (I)-RS+fluoxastrobin;
C14: (I)-RS+kresoxim-methyl;
C15: (I)-RS+picoxystrobin;
C16: (I)-RS+pyraclostrobin;
C17: (I)-RS+trifloxystrobin;
C18: (I)-RS+metrafenone;
C19: (I)-RS+proquinazid;
C20: (I)-RS+mepanipyrim;
C21: (I)-RS+cyprodinil;
C22: (I)-RS+iprodione;
C23: (I)-RS+procymidone;
C24: (I)-RS+carbendazim;
C25: (I)-RS+thiophanate-methyl;
C26: (I)-RS+chlorothalonil;
C27: (I)-RS+fludioxonil;
C28: (I)-RS+benalaxyl-M;
C29: (I)-RS+metalaxyl-M;
C30: (I)-RS+benthiavalicarb;
C31: (I)-RS+cyazofamid;
C32: (I)-RS+cymoxanil;
C33: (I)-RS+dimethomorph;
C34: (I)-RS+mandipropamid;
C35: (I)-RS+valifenalate;
C36: (I)-RS+copper salycilate $C_7H_4O_3.Cu$;
C37: (I)-RS+cuprous oxide $Cu_2O$;
C38: (I)-RS+clothianidin;
C39: (I)-RS+imidacloprid;
C40: (I)-RS+thiacloprid;
C41: (I)-RS+thiamethoxam;
C42: (I)-RS+ethiprole;
C43: (I)-RS+fipronil;
C44: (I)-RS+lambda-cyhalothrin;
C45: (I)-RS+deltamethrin;
C46: (I)-RS+tefluthrin;
C47: (I)-RS+chlorantraniliprole;
C48: (I)-RS+flubendiamide;
C49: (I)-RS+tetraconazole+azoxystrobin;

C50: (I)-RS+tebuconazole+azoxystrobin;
C51: (I)-RS+epoxyconazole+azoxystrobin;
C52: (I)-RS+cyproconazole+azoxystrobin;
C53: (I)-RS+propiconazole+azoxystrobin;
C54: (I)-RS+prothioconazole+azoxystrobin;
C55: (I)-RS+tetraconazole+picoxystrobin;
C56: (I)-RS+tebuconazole+picoxystrobin;
C57: (I)-RS+epoxyconazole+picoxystrobin;
C58: (I)-RS+cyproconazole+picoxystrobin;
C59: (I)-RS+propiconazole+picoxystrobin;
C60: (I)-RS+prothioconazole+picoxystrobin;
C61: (I)-RS+tetraconazole+kresoxim methyl;
C62: (I)-RS+tebuconazole+kresoxim methyl;
C63: (I)-RS+epoxyconazole+kresoxim methyl;
C64: (I)-RS+cyproconazole+kresoxim methyl;
C65: (I)-RS+propiconazole+kresoxim methyl;
C66: (I)-RS+prothioconazole+kresoxim methyl;
C67: (I)-RS+chlorothalonil+azoxystrobin;
C68: (I)-RS+chlorothalonil+picoxystrobin;
C69: (I)-RS+chlorothalonil+pyraclostrobin;
C70: (I)-RS+chlorothalonil+kresoxim methyl;
C71: (I)-RS+copper (II) hydroxide+copper oxychloride;
C72: (I)-RS+copper (II) hydroxide+copper oxychloride+copper salycilate $C_7H_4O_3 \cdot Cu$;
C73: (I)-$R_8S_2$+tetraconazole;
C74: (I)-$R_8S_2$+azoxystrobin;
C75: (I)-$R_8S_2$+benalaxyl;
C76: (I)-$R_9S_1$+tetraconazole;
C77: (I)-$R_9S_1$+azoxystrobin;
C78: (I)-R+tetraconazole;
wherein:
(I)-RS represents the compound of formula (I) in form of racemic mixture,
(I)-$R_8S_2$ represents the compound having the enantiomers R and S in molar ratio R:S=8:2,
(I)-$R_9S_1$ represents the compound having the enantiomers R and S in molar ratio R:S=9:1,
(I)-R represents the enantiomer R in substantially pure form (>99.99 weight %).

Preferably, in said compositions C1-C25, C27-C35, C-38-C48 e C73-C77 the weight ratio of components [A] e [B] ranges from 1:20 to 20:1.

Preferably, in said compositions C26, C36, C37 the weight ratio of components [A] e [B] ranges from 1:20 to a 20:10.

Preferably, in said compositions C49-C69 the weight ratio of component [A] with respect to the two components [B] ([A]: [$B_1$]:[$B_2$]) ranges from 1:20:20 to 20:1:1.

Preferably, in said composition C70 the weight ratio of component [A] with respect to the two components [B] ([A]: [$B_1$]:[$B_2$]) ranges from 1:20:20 to 20:10:1, whereas in C71 the ratio [A]:[$B_1$]:[$B_2$] ranges from 1:20:20 to 20:10:10.

Preferably, in said composition C72, the weight ratio of component [A] with respect to the three components [B] ([A]:[$B_1$]:[$B_2$]:[$B_3$]) ranges from 1:20:20:20 to 20:10:10:10.

As said, the compositions object of the present invention exhibit a strong synergistic effect, which can be evaluated by applying the Colby's formula ("Weeds", 1967, 15, pag. 20-22):

$$E_t = E_A + E_B - (E_A \times E_B / 100)$$

wherein $E_t$ is the expected efficacy percentage for the composition containing the compounds A and B at the dosages $d_A + d_B$, $E_A$ is the efficacy percentage observed for the component A at the dosage $d_A$, $E_B$ is the efficacy percentage observed for the component B at the dosage $d_B$.

When the efficacy observed for the composition A+B ($E_{A+B}$) is higher than the efficacy expected according to the Colby's formula ($E_{A+B}/E_t>1$), there is the presence of a synergistic effect.

In case of ternary combinations, the Colby's formula becomes:

$$E_t = E_A + E_{B1} + E_{B2} - (E_A \cdot E_{B1} + E_A \cdot E_{B2} + E_{B1} \cdot E_{B2}/100) + (E_A \cdot E_{B1} \cdot E_{B2}/10000)$$

wherein $E_t$ is the expected efficacy percentage for the composition containing the compounds A, B1 e B2 at the dosages $d_A + d_{B1} + d_{B2}$, $E_A$ is the efficacy percentage observed for the component A at the dosage $d_A$, $E_{B1}$ is the efficacy percentage observed for the component B1 at the dosage $d_{B1}$, $E_{B2}$ is the efficacy percentage observed for the component B2 at the dosage $d_{B2}$. When the efficacy observed for the composition A+B1+B2 ($E_{A+B1+B2}$) is higher than the efficacy expected according to the Colby's formula ($E_{A+B1+B2}/E_t>1$), there is the presence of a synergistic effect.

Due to the high synergistic effects, the amplitude of the action range, the considerable reduction in resistance phenomena from the target microorganisms, the compositions object of the present invention are endowed with a very high fungicidal activity, which is exerted with respect to numerous phytopathogenic fungi attacking important agricultural crops.

Said compositions exert a fungicidal activity which can be curative, preventive or eradicant, and generally have a very low or null phytotoxicity on the treated crops.

It is therefore a further object of the present invention the use of the synergistic fungicidal compositions described above for the control of phytopathogenic fungi in agricultural crops.

Examples of phytopathogenic fungi that can be effectively treated and fought with the compositions of the present invention, are those belonging to the groups of Basidiomycetes, Ascomycetes, Deuteromycetes or imperfect fungi, Oomycetes: *Puccinia* spp., *Ustilago* spp., *Tilletia* spp., *Uromyces* spp., *Phakopsora* spp., *Rhizoctonia* spp., *Erysiphe* spp., *Sphaerotheca* spp., *Podosphaera* spp., *Uncinula* spp., *Helminthosporium* spp., *Rhynchosporium* spp., *Pyrenophora* spp., *Monilinia* spp., *Sclerotinia* spp., *Septoria* spp. (*Mycosphaerella* spp.), *Venturia* spp., *Botrytis* spp., *Alternaria* spp., *Fusarium* spp., *Cercospora* spp., *Cercosporella herpotrichoides*, *Colletotrichum* spp., *Pyricularia oryzae*, *Sclerotium* spp., *Phytophtora* spp., *Pythium* spp., *Plasmopara viticola*, *Peronospora* spp., *Pseudoperonospora cubensis*, *Bremia lactucae*.

The main crops that can be protected with the compositions according to the present invention comprise cereals (wheat, barley, rye, oats, rice, maize, sorghum, etc.), fruit trees (apples, pears, plums, peaches, almonds, cherries, bananas, grapes, strawberries, raspberries, blackberries, etc.), citrus trees (oranges, lemons, mandarins, grapefruit, etc.), legumes (beans, peas, lentils, soybean, etc.), vegetables (spinach, lettuce, asparagus, cabbage, carrots, onions, tomatoes, potatoes, eggplants, peppers, etc.), cucurbitaceae (pumpkins, zucchini, cucumbers, melons, watermelons, etc.), oleaginous plants (sunflower, rape, peanut, castor, coconut, etc.), tobacco, coffee, tea, cocoa, sugar beet, sugar cane, cotton.

In particular, the compositions of the present invention have proved to be particularly effective in the control of *Plasmopara viticola* on vines, *Phytophtora infestans* and *Botrytis Cinerea* on tomatoes, *Puccinia recondita*, *Erysiphae graminis*, *Helminthosporium teres*, *Septoria nodorum* and *Fusarium* spp. on cereals, in the control of *Phakopsora*

*pachyrhizi* on soybean, in the control of *Uromyces Appendiculatus* on beans, in the control of *Venturia inaequalis* on apple-trees, in the control of *Sphaerotheca fuliginea* on cucumbers.

In addition, the compositions of the present invention are also effective in the control of phytopathogenic bacteria and viruses, such as, for example, *Xanthomonas* spp., *Pseudomonas* spp., *Erwinia amylovora*, the tobacco mosaic virus.

The compositions comprising at least a compound of formula (I) and, as component [B], at least an insecticidal compound selected from one or more of the aforesaid groups of compounds xix-xxv, besides to have an excellent fungicidal activity, also have an excellent insecticidal activity against numerous species of insects harmful to agricultural crops.

It is therefore a further object of the present invention the use of said compositions, comprising at least a compound of formula (I) and at least an insecticidal compound selected from on or more of the aforesaid groups of compounds xix-xxv, for the control of harmful insects in agricultural crops.

Examples of insects which can be controlled with the above said compositions, are those belonging to the order of Hemipthera, Lepidopthera, Tysanopthera, Dipthera, Coleopthera, Orthopthera, Hymenopthera: *Aphis gossypii, Myzus persicae, Macrosiphum euphorbiae, Brevicoryne brassicae, Toxoptera citricidus, Trialeurodes vaporariorum, Bemisia tabaci, Aonidiella aurantii, Comstockaspis perniciosa, Unaspis citri, Psylla piri, Laodelphax striatellus, Nilaparvata lugens, Nephotettix cincticeps, Nephotettix virescens, Chilo suppressalis, Ostrinia* spp., *Spodoptera* spp., *Mamestra brassicae, Agrotis* spp., *Thricoplusia* spp., *Heliothis* spp., *Helicoverpa* spp., *Pieris* spp., *Adoxophyes* spp., *Grapholita molesta, Cydia* spp., *Phyllonorycter blancardella, Lymantria* spp., *Plutella xylostella, Pectinophora gossypiella, Hyphantria cunea, Thrips* spp., *Frankliniella* spp., *Dacus* spp., *Ceratitis capitata, Liriomyza trifolii, Anthonomus grandis, Callosobruchus chinensis, Diabrotica* spp., *Agriotes* spp., *Tribolium* spp., *Locusta migratoria, Oxya* spp., *Solenopsis* spp., *Blattella germanica, Periplaneta* spp.

Even if the components [A] and [B] can be mixed and applied as such on the crops to be protected, for the practical use in agriculture, it is usually preferable to use the fungicidal compositions, according to the present invention, in the form of suitable phytosanitary formulations.

The component [A] and the components [B] can be formulated separately and mixed in the preselected diluent (for example water) at the moment of the treatment of the agricultural crops to be protected, or combined together in single formulation ready to use before treatment.

Both in the case of components formulated separately, and in the case of components [A] and [B] combined together in formulations ready to use, the formulations can be in the form of dry powders, wettable powders, emulsifiable concentrates, emulsions, micro-emulsions, pastes, granules, water-dispersible granules, solutions, suspensions, etc.: the selection of the type of formulation depends both on the characteristics of components A and B, and on the specific use.

The compositions are prepared with known methods, for example by diluting the active ingredients with a solid or liquid diluent, possibly in the presence of surfactants, dispersers, suspending agents, stabilizers, adjuvants, etc.

The following can be used, for example, as solid diluent or carriers: silica, kaolin, bentonite, talc, diatomaceous earth, dolomite, calcium carbonate, magnesia, gypsum, clays, synthetic silicates, attapulgite, seppiolites.

The following can be used, for example, as solvents or liquid diluents, in addition to water, aromatic organic solvents (xyloles or alkylbenzole mixtures, chlorobenzene, etc.), paraffins (oil cuts), alcohols (methanol, propanol, butanol, octanol, glycerol, etc.), esters (ethyl acetate, isobutyl acetate, alkyl carbonates, alkyl esters of adipic acid, alkyl esters of glutaric acid, alkyl esters of succinic acid, alkyl esters of lactic acid, etc.), vegetable oils (rapeseed oil, sunflower oil, soybean oil, castor oil, corn oil, peanut oil, and their alkyl esters), ketones (cyclohexanone, acetone, acetophenone, isophorone, ethyl amyl ketone, etc.), amides (N, N-dimethylformamide, N-methylpyrrolidone, etc.), sulfoxides and sulfones (dimethylsulfoxide, dimethyl-sulfone, etc.) and mixtures thereof.

Surfactants that can be used are sodium salts, calcium salts, potassium salts, triethylamine or triethanolamine of alkylnaphthalensulfonates, polynaphthalenesulfonates, alkylsulfonates, aryl-sulfonates, alkylarylsulfonates, polycarboxylates, sulfosuccinates, alkylsulfosuccinates, lignin sulfonates, alkyl sulfates; and again polyethoxylated fatty alcohols, polyethoxylated alkyl phenols, polyethoxylated esters of sorbitol, polyethoxylated polypropoxy (block copolymers), can be used.

The compositions can also contain special additives for particular purposes, for example antifreeze agents such as propylene glycol, or adhesives such as Arabic gum, polyvinyl alcohol, polyvinylpyrrolidone, etc.

If desired, other active ingredients compatible with [A] and [B] can be added to the compositions, such as, for example, further fungicidal or insecticidal compounds different from components [B] described above, phytoregulators, antibiotics, herbicides, fertilizers and/or mixtures thereof.

Examples of fungicides, other than components [B], that can be included in the synergistic compositions object of the present invention are listed hereunder with their international ISO name: ampropylfos, anilazine, benodanil, blasticidin-S, bupirimate, buthiobate, chinomethionat, chloroneb, chlozolinate, debacarb, dichlone, diclobutrazol, diclomezine, dicloran, diclocymet, diethofencarb, diflumetorim, dimethirimol, dinocap, dipyrithione, ditalimfos, dithianon, edifenphos, ethirimol, ethoxyquin, etridiazole, fenaminosulf, fenapanil, fenarimol, fenfuram, fenoxanil, fentin, ferbam, ferimzone, fluoroimide, fluotrimazole, flusulfamide, hymexazol, hydroxy-quinoline sulfate, iprobenfos, isoprothiolane, kasugamycin, mancopper, mebenil, mepronil, meptyldinocap, methfuroxam, metiram, metsulfovax, natamycin, nitrothal-isopropyl, nuarimol, ofurace, oxadixyl, pefurazoate, pencycuron, pentachlorofenol and its salts, phthalide, piperalin, polyoxins, propamocarb, prothiocarb, pyracarbolid, pyrazophos, pyribencarb, pyrifenox, pyroquilon, pyroxyfur, quinacetol, quinazamid, quintozene, streptomycin, thiadifluor, thicyofen, thiram, tioxymid, tolclofos-methyl, triarimol, triazbutil, triazoxide, tricyclazole, triforine, validamycin, vinclozolin, ziram, sulfur.

The total concentration of components [A] and [B] in said compositions can vary within a wide range; it generally ranges from 1% to 99% by weight with respect to the total weight of the composition, preferably from 5% to 90% by weight with respect to the total weight of the composition.

In order to protect the agricultural crops, the compositions object of the present invention can be applied to any part of the plant, or on the seeds before sowing, or on the ground in which the plant grows.

A further object of the present invention therefore relates to a method for the control of phytopathogenic fungi in agricultural crops, which comprises applying an effective dose of at least one synergistic fungicidal composition of the type described above on one or more parts of the plant to be protected (for example, on seedlings, leaves, fruits, stems, branches, roots) and/or on the seeds of said plants before sowing, and/or on the ground in which the plant grows.

A further aspect of the present invention is a method for the control of harmful insects in agricultural crops which comprises applying an effective dose of at least one synergistic fungicidal composition comprising at least a compound of formula (I) and at least an insecticidal compound selected from one or more of the groups of compounds xix-xxv described above, on one or more parts of the plant to be protected (for example, on seedlings, leaves, fruits, stems, branches, roots) and/or on the seeds of said plants before sowing, and/or on the ground in which the plant grows.

Preferred way of application for the compositions comprising the compound (I) and at least an insecticidal compound selected from one or more groups of compounds xix-xxv is the seed-dressing.

The total amount of components [A] and [B] to be applied in order to obtain the desired effect can vary according to different factors such as, for example, the compounds used, the crop to be preserved, the type of pathogen or insect, the degree of infection, the climatic conditions, the application method, the formulation used.

Overall doses of components [A] and [B] ranging from 10 g to 5 kg per hectare of agricultural crop generally provide a sufficient control.

The following examples are provided for a better understanding of the invention, which should be considered as being illustrative and non-limiting of the same.

EXAMPLE 1

Preparation of the 3-difluoromethyl-N-(7-fluoro-1,1,3-trimethyl-4-indanyl)-1-methyl-4-pyrazolecarboxamide (I)

A solution of 40 g of 3-(difluoromethyl)-1-methyl-1H-pyrazole-4-carbonyl chloride [compound of formula (III); MW 194.5] in 40 ml of dichloroethane, is dropped at room temperature in a solution of 34 g of 6-fluoro-2,2,4-trimethyl-1,2,3,4-tetrahydroquinoline [compound of formula (V); MW 193] and 30 ml of triethylamine in 200 ml of dichloroethane.

After stirring for 3 hours at reflux, the reaction mixture is poured in water (1.2 l) and extracted with dichloroethane. The organic layer is washed with 10% aqueous hydrochloric acid, anhydrified with sodium sulfate, concentrated under vacuum to afford 58 g of a crude solid product corresponding to N-(3-difluoromethyl-1-methyl-1H-4-pyrazolecarbonyl)-6-fluoro-2,2,4-trimethyl-1,2,3,4-tetrahydroquinoline [compound of formula (II); GC-mass: $M^+=351$].

To this crude product, 165 ml of 85% aqueous sulfuric acid are added and the mixture is then heated under stirring at 60° C. for 30 minutes. After cooling the mixture is poured into water and ice, and extracted with dichloromethane. The organic layer is then washed with water, with a saturated solution of sodium bicarbonate in water, and with a saturated solution of sodium chloride in water. The organic layer is anhydrified with sodium sulfate and concentrated under vacuum: the residue is purified by chromatography on silica gel (eluent heptane/EtOAc 6:4) to give 48 g of a white solid with melting point 147° C., corresponding to the desired product in racemic form, (I)-RS. GC-mass: $M^+=351$.

$^1$H NMR (200 Mhz, CDCl$_3$) δ at: 1.43 (3H, d), 1.38 (3H, s), 1.44 (3H, s), 1.66 (1H, dd), 2.21 (1H, dd), 3.38 (1H m), 3.98 (3H, s), 6.81 (1H, bs), 6.95 (1H, t), 6.70. (1H, m), 7.81 (1H, bs), 8.03 (1H, bs)

EXAMPLE 2

Preparation of Separated Enantiomers of Compound (I)

36.8 g (1 eq) of racemic 7-fluoro-1,1,3-trimethyl-4-aminoindane [compound (IV)] and 14.3 g (0.5 eq) of D-(2S, 3S)-(−)-tartaric acid in methanol (30 ml) were mixed and heated at 70° C. for 1 hour.

The mixture was left to cool to room temperature; a precipitate was formed and the mixture kept for one night at 4° C. The formed solid was filtered off, washed with a small amount of methanol and re-crystallized from methanol for six times to afford 14.8 g of an off white solid, corresponding to the 7-fluoro-1,1,3-trimethyl-4-aminoindane D-tartarate.

To the salt, a 5% sodium hydroxide aqueous solution was added until pH≥10, and the mixture extracted three times with diethyl ether. The reunited organic layers were washed with water and brine. Then, dried over Na$_2$SO$_4$ and concentrated under reduced pressure to obtain 6.38 g of (−)-4-amino-7-fluoro-1,1,3-trimethylindane as a white powder (yield 17%); e.e. >99% (HPLC).

To a solution of 600 mg of 3-difluoromethyl-1-methyl-1H-pyrazole-4-carboxylic acid [compound (III)] and a catalytic amount of N,N-dimethylformamide in dichloromethane (7 mL), 450 mg of thionyl chloride were added dropwise. The mixture was refluxed for 2 h. The reaction was monitored by GC/MS. The solvent was evaporated in vacuo. The crude acid chloride obtained was used in the following step.

A solution of the crude 3-difluoromethyl-1-methyl-1H-pyrazole-4-carbonyl chloride in dichloroethane (6 mL) was added dropwise over a period of 10 minutes, under nitrogen atmosphere, to a solution of 660 mg of (−)-4-amino-7-fluoro-1,1,3-trimethylindane, a catalytic amount of 4-dimethylaminopyridine and 420 mg of triethylamine in dichloroethane (5 mL).

The mixture was stirred at room temperature overnight. At completion of the reaction (monitored through GC-MS) the mixture was diluted with dichloromethane (20 mL) and cooled at 0° C.; a solution (20 mL) of 5% HCl was added.

The layers were separated and the organic phase washed with 5% HCl solution (2×20 mL), water (2×20 mL) and brine, then dried over Na$_2$SO$_4$. The solvent was evaporated under reduced pressure to give 1.3 g of a pale yellow solid.

The crude product was purified by column chromatograpy (eluent: heptane/EtOAc 6:4) to give 1.1 g (yield 92%) of 99.5% pure enantiomer (−) (e.e. >99% determined by HPLC with chiral column) as a white solid with m.p.=129-130° C.

GC-MS: $M^+=351$; $[\alpha]_D^{20}=-59.5°$ (CHCl$_3$, 1 g/100 ml).

In analogous manner, starting from racemic 7-fluoro-1,1,3-trimethyl-4-aminoindane [compound (IV)] and L-(2R, 3R)-(+)-tartaric acid, the 99.3% pure enantiomer (+) was prepared (e.e. >99% determined by HPLC with chiral column): white solid with m.p.=131-132° C.

GC-MS: $M^+=351$; $[\alpha]_D^{20}=+60.1°$ (CHCl$_3$, 1 g/100 ml).

EXAMPLE 3

Determination of "In Vitro" Activities of Racemic (I) and Enantiomers Against Phytopathogenic Microorganisms Under sterile conditions, the technical racemic (I), the (−) and (+) enantiomers (prepared in Example 2) under testing, were dissolved in dimethylsulfoxide and serially diluted 3-fold to obtain a growth inhibition curve. Aqueous treatment solutions were prepared by adding DMSO stocks to water and mixing by pipet resulting in 2× final treatment concentration and 2× final DMSO concentration of 1.6%.

Sporulating plates of phytopathogenic microorganisms were harvested under sterile conditions in strength Potato Dextrose Broth. Spores were filtered with cheesecloth and diluted to about 40000 spores per ml. Spores were aliquoted into 96 well microtiter plates at 150 microliters of spore suspension per well. Pathogenic spore suspensions were then treated with the 2× aqueous treatment solution or 1.6% DMSO for controls to give 1× final concentration or 0.8% DMSO. Plates were then held for 43 hours at room temperature.

After 43 hours at room temperature, plates were visually assessed microscopically for spore germination and growth inhibition. Plates were also quantitatively measured for growth inhibition by measuring optical density on a spectrophotometric plate reader at 405 nanometer wavelength. Optical density was corrected for absorbance of the media and active ingredient by subtracting the 405 nm readings for the 2× aqueous treatment solution or DMSO solution diluted with ½ strength POTATO DEXTROSE BROTH and no spores.

The % growth inhibition of the pathogen obtained for the technical racemic (I), (−) and (+) enantiomers was calculated according to the formula:

Percent Inhibition=((1−(OD trt−OD trt blank)/OD untreated−OD untreated blank))×100)

wherein OD trt is the optical density at 405 nm for the spore suspension plus aqueous treatment solution and OD trt blank is the optical density at 405 nm for the 2× aqueous treatment solution plus ½ strength POTATO DEXTROSE BROTH and no spores and OD untreated is the optical density at 405 nm for the spores plus 1.6% DMSO and OD untreated blank is the optical density at 405 nm for the 1.6% DMSO plus strength POTATO DEXTROSE BROTH and no spores. Values are the average of three replicates. Concentrations of the racemic, (−) and (+) enantiomers giving 50% growth inhibition (pI50) were calculated using GraphPad Prism software Percent inhibition values were calculated using GraphPad Prism software Version 4.

Microorganisms tested were *Botrytis cinerea* (BC), *Stagonospora nodorum* (SN) and *Magnaporthe griseae* (MG).

The results are reported in Table 1.

TABLE 1

| Compound | BC pI50 (ppm) | SN pI50 (ppm) | MG pI50 (ppm) |
| --- | --- | --- | --- |
| Racemic (I) | 0.32 | 1.1 | 0.72 |
| (−)-(I) | 0.17 | 0.42 | 0.46 |
| (+)-(I) | n.i. | 72 | 4.6 | n.i. = no inhibition

EXAMPLE 4

Determination of the Fungicidal Activity in Preventive Application (5 Days) Against *Puccinia recondite* on Wheat Leaves of wheat plants of the Salgemma variety, grown in pots in a conditioned environment kept at 20° C. and 70% of relative humidity (R.H.), were treated by spraying both sides of the leaves with the compounds and the compositions under testing, dispersed in hydroacetonic solutions at 20% by volume of acetone.

After remaining 5 days in a conditioned environment, the plants were sprayed on both sides of the leaves with an aqueous suspension of conidia of *Puccinia recondita* (2 mg of inoculum per 1 ml of solution for infection).

After being sprayed, the plants were kept in a humidity-saturated environment at a temperature ranging from 18 to 24° C. for the incubation period of the fungus (1 day).

After this period, the plants were put in a greenhouse with R.H. of 70% and at a temperature of 18-24° C. for 14 days.

At the end of this period the external symptoms of the pathogen appeared and it was therefore possible to proceed with the visual assessment of the intensity of the infection. The fungicidal activity was expressed as percentage of reduction of affected leaves areas with respect to those of untreated plants used as control: the scale comprised, as extremes, the value 100 (full activity; healthy plant) and the value 0 (no activity; completely infected plant).

At the same time, the phytotoxicity (percentage of leaf necrosis) induced on the wheat plants by the application of the products and compositions was evaluated: in this case, the scale ranged from 0 (no phytotoxicity) to 100 (completely necrotized plant).

In Table 2, the activities of racemic (I) and pure enantiomers of compound (I), prepared in Example 2, are reported.

TABLE 2

| Compound | Rate (ppm) | % Activity | % Phytotoxicity |
| --- | --- | --- | --- |
| Racemic (I) | 125 | 98 | 0 |
|  | 62.5 | 96 | 0 |
| (−)-(I) | 125 | 100 | 0 |
|  | 62.5 | 96 | 0 |
| (+)-(I) | 125 | 45 | 0 |
|  | 62.5 | 20 | 0 |

The synergism of the compositions (A+B) under testing was evaluated according to the Colby's formula:

$E_t = E_A + E_B - (E_A \times E_B / 100)$ wherein $E_t$ is the expected efficacy percentage for the composition containing the compounds A and B at the dosages $d_A + d_B$, $E_A$ is the efficacy percentage observed for the component A at the dosage $d_A$, $E_B$ is the efficacy percentage observed for the component B at the dosage $d_B$.

When the efficacy observed for the composition A+B ($E_{A+B}$) is higher than the efficacy expected according to the Colby's formula ($E_{A+B}/E_t > 1$), a synergistic effect is confirmed.

EXAMPLE 5

Determination of Synergistic Effects "In Vitro" Against Phytopathogenic Microorganisms Under sterile conditions, the products and the compositions under testing were dissolved in dimethylsulfoxide, diluted with water and added under vigorous stirring to POTATO DEXTROSE AGAR, kept in a thermostatic bath at 55° C. The AGAR preparations, containing the compounds and the compositions under testing at the desired rates, were poured into 60 mm diameter Petri dishes (three for each product and composition) and left to cool to ambient temperature.

After solidification of the agarized medium, AGAR disks having 6 mm of diameter and supporting the micelyum of the microorganism, were placed in the centre of the Petri dishes; Petri dishes containing untreated POTATO DEXTROSE AGAR were also inoculated with the microorganism and used as control.

After incubation at 28° C., when control colonies had grown over 30 mm in diameter, but without reaching the edge of the dishes, the diameters of the developed colonies in treated and untreated dishes were measured; the percentage growth inhibition of the microorganism obtained with products and compositions was calculated according to the formula:

$$I = (1 - z_1/z_0) \times 100$$

wherein $z_1$ is the diameter (average of three replicates) of the colonies treated with compounds and mixtures and $z_0$ is the diameter (average of three replicates) of untreated colonies.

Microorganisms tested were *Botrytis cinerea, Fusarium culmorum, Helminthosporium teres, Pyricularia oryzae, Septoria nodorum, Venturia inaequalis.*

The synergism of a binary mixture (A+B) at the dose $(d_A + d_B)$ was evaluated according to the Colby's formula:

$$I_t = I_A + I_B - (I_A \times I_B / 100)$$

wherein:
$I_t$ is the % growth inhibition expected for the mixture; $I_A$ is the % growth inhibition observed for compound A at the dose $d_A$; $I_B$ is the % growth inhibition observed for compound B at the dose $d_B$.

When the % growth inhibition observed for the composition (A+B) is higher than that calculated by the Colby's formula ($I_{A+B} > I_t$; $I_{A+B}/I_t > 1$), a synergistic effect is confirmed.

The invention claimed is:

1. A composition for the protecting of agrarian crops comprising:
   at least one component [A], consisting of the compound having formula (I), 3-difluoromethyl-N-(7-fluoro-1,1,3-trimethyl-4-indanyl)-1-methyl-4-pyrazolecarboxamide

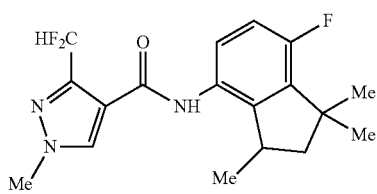

(I)

wherein Me is a methyl group, and
at least one component [B] which is an azole selected from the group consisting of azaconazole, bitertanol, bromuconazole, cyproconazole, difenoconazole, epoxyconazole, fenbuconazole, fluquinconazole, flusilazole, flutriafol, hexaconazole, imazail, ipconazole, metconazole, myclobutanil, penconazole, propiconazole, prochloraz, prothioconazole, simeconazole, tebuconazole, tetraconazole, triadimefon, triadimenol, triflumizole, and triticonazole.

2. The composition according to claim 1, wherein said one or more components [B] are selected from
   cyproconazole, difenoconazole, epoxyconazole, flutriafol, penconazole, prochloraz, prothioconazole, tebuconazole, and tetraconazole.

3. The composition according to claim 1, wherein said compound having formula (I) is a racemic mixture (I RS).

4. The composition according to claim 1, wherein said compound having formula (I) is selected from:
   (a)—a mixture having one of the enantiomers-in a weight ratio of 51:49 to 99.99:0.01, by weight and
   (b)—one of the two enantiomers R ((I)-R) or S ((I)-S) in a substantially pure form.

5. The composition according to claim 4, wherein said compound having formula (I) is
   a mixture enriched in the enantiomer R, wherein
   the enantiomer R has a purity of >99.99% by weight.

6. The composition according to claim 1, wherein the weight ratio between said at least one component [A] and said at least one component [B] ranges from 1:20 to 20:1.

7. The composition according to claim 1, which comprises a composition selected from the group consisting of
   RS tetraconazole;
   RS tebuconazole;
   RS cyproconazole;
   RS difenoconazole;
   RS epoxyconazole;
   RS flutriafol;
   RS penconazole;
   RS prothioconazole;
   RS prochloraz;
   —$R_8S_2$ tetraconazole;
   —$R_9S_1$ tetraconazole;
   and
   R tetraconazole;
   wherein:
   —RS indicates a compound of component [A] in the form of a racemic mixture,
   —$R_8R_2$ indicates a compound of component [A] containing the enantiomers R and S in a molar ratio R:S=8:2,
   —$R_9R_1$ indicates a compound of component [A] containing the enantiomers R and S in a molar ratio R:S=9:1, and
   —R indicates an enantiomer R of a compound of component [A] in substantially pure form.

8. The composition according to claim 1, wherein said at least one component [A] and said at least one component [B], together or separately, are diluted with one or more solid or liquid diluents, with the addition of one or more surfactants, dispersing agents, suspending agents, stabilizers, adjuvants, anti-freeze agents or adhesion agents.

9. The composition according to claim 8, comprising at least a further active principle, compatible with said components [A] and [B], selected from the group consisting of phytoregulators, antibiotics, herbicides, fertilizers and mixtures thereof.

10. The composition according to claim 1, wherein said at least one component [A] and said at least one component [B], together or separately, are diluted with one or more solid or liquid diluents, dispersing agents, suspending agents, stabilizers, adjuvants, anti-freeze agents or adhesion agents.

11. A composition for the protection of agrarian crops as defined in claim 1 having active ingredients which consist of:

at least one component [A], consisting of the compound having formula (I) 3-difluoromethyl-N-(7-fluoro-1,1,3-trimethyl-4-indanyl)-1-methyl-4-pyrazolecarboxamide:

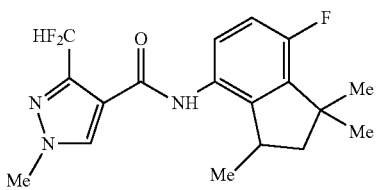

(I)

wherein Me is a methyl group, and an azole selected from the group consisting of azaconazole, bitertanol, bromuconazole, cyproconazole, difenoconazole, epoxyconazole, fenbuconazole, fluquinconazole, flusilazole, flutriafol, hexaconazole, imazail, ipconazole, metconazole, myclobutanil, penconazole, propiconazole, prochloraz, prothioconazole, simeconazole, tebuconazole, tetraconazole, triadimefon, triadimenol, triflumizole, and triticonazole.

12. A composition for the protection of agrarian crops as defined in claim 11 where the azole is selected from the group consisting of prochloraz, prothioconazole and tetraconazole.

13. A method for the control of phytopathogenic fungi in agricultural crops which comprises applying an effective amount of a composition according to claim 1 to an agricultural crop.

14. The method for the control of phytopathogenic fungi according to claim 13 where said phytopathogenic fungi are selected from the following groups: Basidiomycetes, Ascomycetes, Deuteromycetes or imperfect fungi, Oomycetes: *Puccinia* spp., *Ustilago* spp., *Tilletia* spp., *Uromyces* spp., *Phakopsora* spp., *Rhizoctonia* spp., *Erysiphe* spp., *Sphaerotheca* spp., *Podosphaera* spp., *Uncinula* spp., *Helminthosporium* spp., *Rhynchosporium* spp., *Pyrenophora* spp., *Monilinia* spp., *Sclerotinia* spp., *Septoria* spp. (*Mycosphaerella* spp.), *Venturia* spp., *Botrytis* spp., *Alternaria* spp., *Fusarium* spp., *Cercospora* spp., *Cercosporella herpotrichoides*, *Colletotrichum* spp., *Pyricularia oryzae*, *Sclerotium* spp., *Phytophtora* spp., *Pythium* spp., *Plasmopara viticola*, *Peronospora* spp., *Pseudoperonospora cubensis*, *Bremia lactucae*.

15. The method for the control of phytopathogenic fungi according to claim 13 wherein the agrarian crops are selected from: cereals, fruit trees, citrus fruits, legumes, horticultural crops, cucurbits, oleaginous plants, tobacco, coffee, tea, cocoa, sugar beet, sugar cane, cotton.

16. A method for controlling phytopathogenic fungi in agrarian crops, which comprises applying an effective dose of at least one synergistic composition according to claim 1, on one or more parts of the plants to be protected and/or on the seeds of said plants before sowing and/or on the ground in which said plants grow.

* * * * *